Figure 1A:
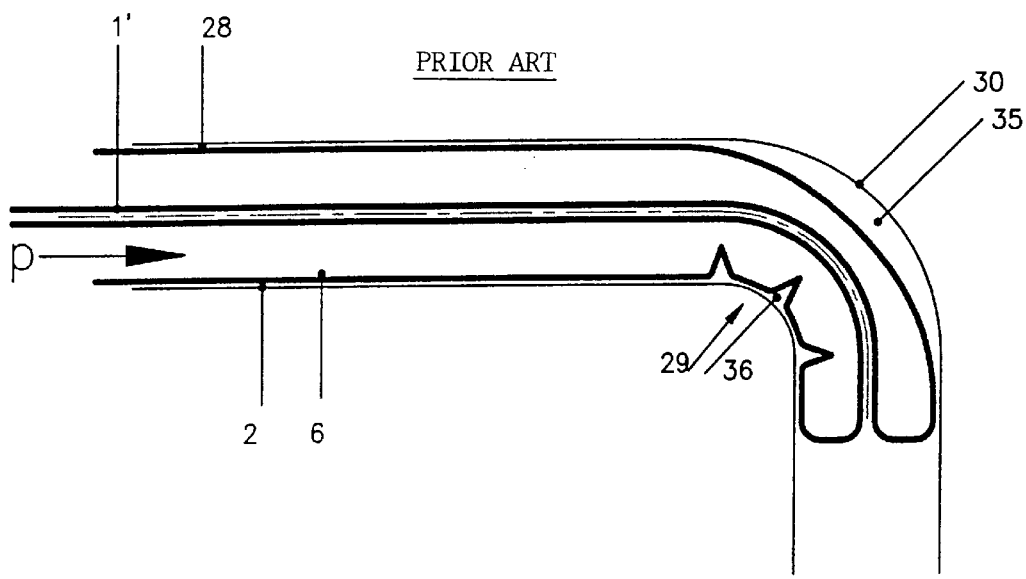

United States Patent
Schwert et al.

[11] Patent Number: 6,129,119
[45] Date of Patent: Oct. 10, 2000

[54] FLEXIBLE TUBE FOR LINING PIPES AND DUCTS AS WELL AS METHOD AND AN APPARATUS FOR MANUFACTURING THEREOF

[75] Inventors: Siegfried Schwert; André Rose; Andreas Hüttemann; Peter Marquardt; Wolf Rabold, all of Berlin, Germany

[73] Assignee: Karl Weiss Hoch - Tief - und Rohrleitungsbau GmbH & Co., Germany

[21] Appl. No.: 09/151,511

[22] Filed: Sep. 11, 1998

[51] Int. Cl.[7] ......................................... F16L 55/16
[52] U.S. Cl. .............. 138/98; 138/97; 264/269; 156/287; 405/150.1
[58] Field of Search ............ 138/98, 97; 156/287; 428/36.1; 264/269

[56] References Cited

U.S. PATENT DOCUMENTS

| | | | |
|---|---|---|---|
| 4,576,205 | 3/1986 | Morinaga et al. | 138/98 |
| 4,681,783 | 7/1987 | Hyodo et al. | 138/98 X |
| 4,877,665 | 10/1989 | Higuchi et al. | 138/98 X |
| 5,077,107 | 12/1991 | Kaneda et al. | 138/98 X |
| 5,535,786 | 7/1996 | Makela et al. | 138/98 |

*Primary Examiner*—Patrick Brinson
*Attorney, Agent, or Firm*—Locke Reynolds LLP

[57] ABSTRACT

A flexible tube for lining pipes and ducts as well as a method and an apparatus for manufacturing thereof are suggested. The flexible tube is composed of a coated fabric of high resilient warp threads as well as woof threads having lower elasticity. With the flexible tube thus suggested, strong curvatures or angles being present in the pipes can be lined without wrinkles and all-over for the first time.

This is enabled in that the high resilient warp threads are stabilized by covering yarn upon straight pipe portions and hence comprise a limited linear extension such that the flexible tube can be placed inside the pipe in quality.

In the curved pipe portions the high elasticity of the basic warp thread is activated by a force increase during passing through these portions by compensating the forces of the covering yarn, such that the flexible tube closely fits to the inner pipe wall, all-over and without any wrinkles in these regions.

The coating of the high resilient yarn is enabled by means of a new coating technique.

22 Claims, 4 Drawing Sheets section C – C:
fabric in depressurized condition section C – C:
fabric in pressurized condition

Fig. 4b (Detail X)

FLEXIBLE TUBE FOR LINING PIPES AND DUCTS AS WELL AS METHOD AND AN APPARATUS FOR MANUFACTURING THEREOF

The present invention relates to a flexible tube for lining pipes and ducts as well as a method and an apparatus for manufacturing thereof.

It is well known to introduce outside coated flexible tubes for lining a pipe with an opening at the beginning of said pipe in a turning inside out manner into said pipe, wherein the outer surface of the flexible tube is turned inside out and forms the inner wall of the redeveloped pipe. However, such flexible tube may also be introduced by means of introducing (without turning inside out) into a pipe or duct.

However, with prior art flexible tubes, particularly with smaller pipe diameters, it is not possible for smallest pipe bends and elbows to be lined wrinkle-free as well. With flexible tubes according to the prior art, in these cases upsetting wrinkles are formed in the region of knees whereby the conditions for media to be led through are highly deteriorated. Thus, at such locations high pressure losses are caused with gaseous medias and strong turbulences originate with liquid medias and with sewerage drains deposits may result in clogging in such upsetting wrinkles. Due to the formation of upsetting wrinkles, hitherto the application of the flexible tubes mentioned above, which are to be introduced by turning up method, has only been enabled when it bargains for linear pipes sections or pipe bends having a large pipe diameter and large radi, respectively.

Coming from this prior art, it is the object of the present invention to provide a flexible tube for lining pipes and ducts as well as a method and an apparatus for manufacturing thereof which may also be installed wrinkle-free in the narrow bends with less pipe diameters such as ocuring with service lines for gas and drinking water, respectively, or sewage water.

This object is solved with respect to the flexible tube according to claim 1 and with respect to the manufacturing method according to claim 22 as well as with respect to the apparatus for manufacturing the flexible tube according to claim 30.

As a result of comprising the flexible tube of coated fabric made of high resilient warp threads as well as of woof threads having lower elasticity, it is possible with the arrangement of the longitudinal flexible tube axis towards the longitudinal axis of the warp threads to provide a flexible tube of high linear extension. With this, narrowest curvatures of pipes can often be nearly lined wrinkle-free. This is because the side flexible tube portion being in a region more distant from the center of curvature can be more stretched because of the improved linear extension of the flexible tube, such that a flat lining of the inner pipe wall may also result within the range of this outer curvature. In addition, with the turning up method performed with pressure, high elasticity of the warp threads allows lower "reversing pressures" for turning up said flexible tube.

The linear extension of the flexible tube according to the invention is particularly high, when this is produced by the manufacturing method according to the invention and the manufacturing apparatus according to the invention.

As a result of pressing plastic melting into a chamber for manufacturing the flexible tube and guiding a flexible tube blank being not supported in the interior along its longitudinal axis through the chamber, wherein the outer surface of the flexible tube blank is coated with plastic melting, a high elasticity of said high resilient warp threads being preferably longitudinally disposed, remains largely maintained after the coating process as well. Nevertheless, the quality of the coating is very high. Bubbling inside the coating such as with dipping methods does not occur because of the pressurized impress of the plastic melting, which can affect an impairment of the density of the flexible tube.

Contrary to the flat coating, wherein a flat folded flexible tube is deposited with a coating on the upper and lower sides, the quality is significantly improved with the manufacturing method according to the invention. The reason for that is as follows: With the conventional flat coating comprising a subsequent coating of the side edges, on the one hand, it is possible for the flexible tube coating to be carried out significantly beyond the flexible tube width and the laterally protruding part to be severed in a further operation (this is lavishly and insufficiently in quality, however). Alternatively, with conventional flat coating, the missing coating can be deposited in the region of the side edges by displacing and turning the flexible tube, respectively, and by later subsequent coating of the former side edge being flat laying. Here, a doubling and thus an unsymmetrical coating thickness is formed, however, such that later closely fitting of the flexible tube in the inner pipe wall is not possible even with swelling the flexible tube under a high pressure load (there is even the danger of travelling behind and even with swelling the flexible tube under a high pressure load (there is even the danger of travelling behind and defective revovation, respectively). Since the transversal elasticity is lesser in the doubling region, there is highly anger, that the flexible tube does not fit closely in this region.

On the contrary, with coating methods according to the prior art by means of extrusion tools a flexible tube blank is drawn over a respective mandrel to maintain its circular cross-section during depositing the plastic melting on the outer surface of the flexible tube blank. However, by the external pressure of the plastic melting, here the flexible tube blank is radially pressed with a high pressure against the mandrel, such that high tensile forces in the longitudinal direction of the flexible tube blank are required to draw said flexible tube blank through the extrusion tool. Due to this tension load of the flexible tube blank a high linear extension of the flexible tube blank occurs during the coating process. This results in that the linear extension of the flexible tube blank is "frozen" as it were with cooling of the plastic melting deposited as coating such that in the cooled condition the coated flexible tube merely comprises a low residual extensibility in the longitudinal direction.

Advantageous embodiments of the present invention will be described in the reamining claims.

Another modification of the invention provides that the flexible tube to be coated is not a woven flexible tube but a knitted fabric of high resilient yarn (i.e. manufactured by a knitting method). with this it is possible to produce a fabric flexible tube having high linear and transversal extensions by means of a single yarn type.

An advantageous embodiment of the fabric flexible tube according to the invention provides the ratio of the warp threads $\epsilon_{max}$ to the woof threads $\epsilon_{max}$ to be in the range of 1.1 to 50. Despite of the indicated numeral ratio a sufficient elasticity of the woof threads still results, which is also responsible for the transversal extensibility of the coated flexible tube. This transversal extensibility, which is required to previously reach a complete close fitting of the flexible tube against the pipe wall with previously lower reversing pressures, is constantly accomplished hence with a flexible tube according to the invention.

A particularly advantageous embodiment of the invention provides a warp thread to be composed of a basic warp thread wrapped with a covering yarn, wherein the basic warp thread comprises a length related mass within the range of 22 to 3000 dtex, and the covering yarn comprises a length related mass of 44 to 1000 dtex (1 dtex=0.1 milligram per meter. As for the basic warp thread and covering yarn polyurethane and polyester or polyamide are advantageous materials. With this, a not solved problem with lining pipes having straight and curved portions is solved. This problem existed in that with straight pipe portions (in order to enable a controlled drive) a great linear extension was not desired, however, was desirably in the region of curvatures. The flexible tube according to the invention having a basic warp thread and covering yarn as well with this comprises a limited linear extension to ensure a controlled introducing the flexible tube inside straight pipe portions, since the covering yarn stabilizes the basic warp thread. By virtue of a high resilient basic warp thread, however, in curvatures, in which an extension of the flexible tube is required for plane close fitting of the flexible tube against the inner pipe wall, a sufficient extensibility of the flexible tube is given, which is activated by means of force increase while advancing through the pipe bends.

Another advantageous development of the invention provides the coating of the flexible tube to be radially introduced only to a part, e.g. the half thickness of the fabric. With this a other hand, by means of adhesives for fitting the flexible tube to the pipe wall are enabled.

Another advantageous embodiment provides the chamber to have a substantially ellipsoidal cross-section corresponding to the cross-section of the flexible tube blank being compressed due to the pressure of the plastic melting for depositing the plastic melting upon a flexible tube blank transversally to the longitudinal direction of a flexible tube blank being led through. Because of this the chamber is adapted to the cross-section geometry of the flexible tube, such that the ways of the plastic melting from the chamber walls toward the outer flexible tube surface are maintained small and clearance volumes of the plastic melting can be avoided.

A particularly advantageous embodiment provides the melting pipes leading in the interior of the chamber to be constructed as a circular distributor means during its course inside the chamber, thus in its end portion being directed toward the flexible tube blank. Here, the plastic melting is supplied from several locations being distributed over the periphery of the cross-section of the flexible tube blank such that a uniform coating being uniformly over the periphery of the flexible tube blank can be ensured.

Further advantageous embodiments of the present invention will be given in the remaining claims.

Figure 1B:
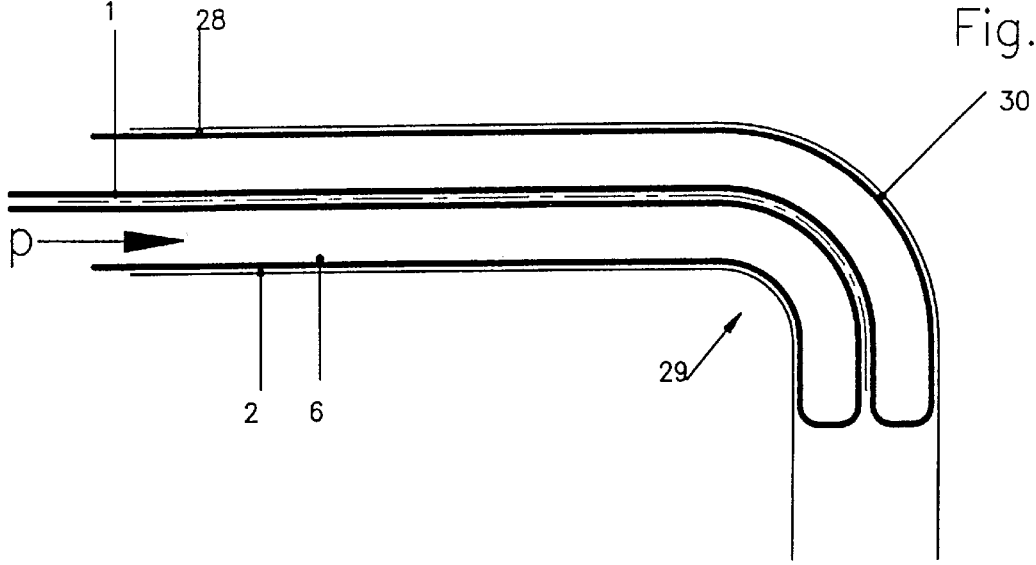
Figure 2A:
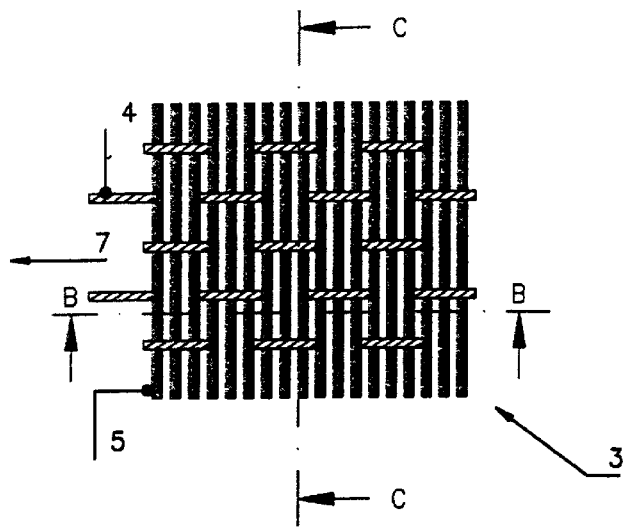
Figure 2B:
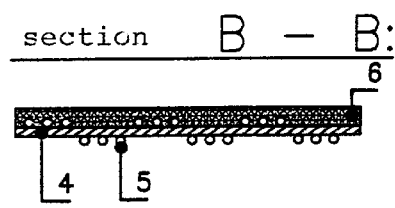
Figure 2C:
Figure 2D:
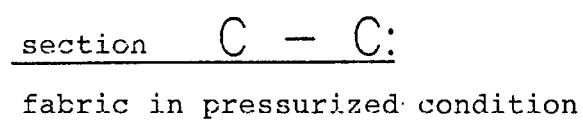
Figure 3:
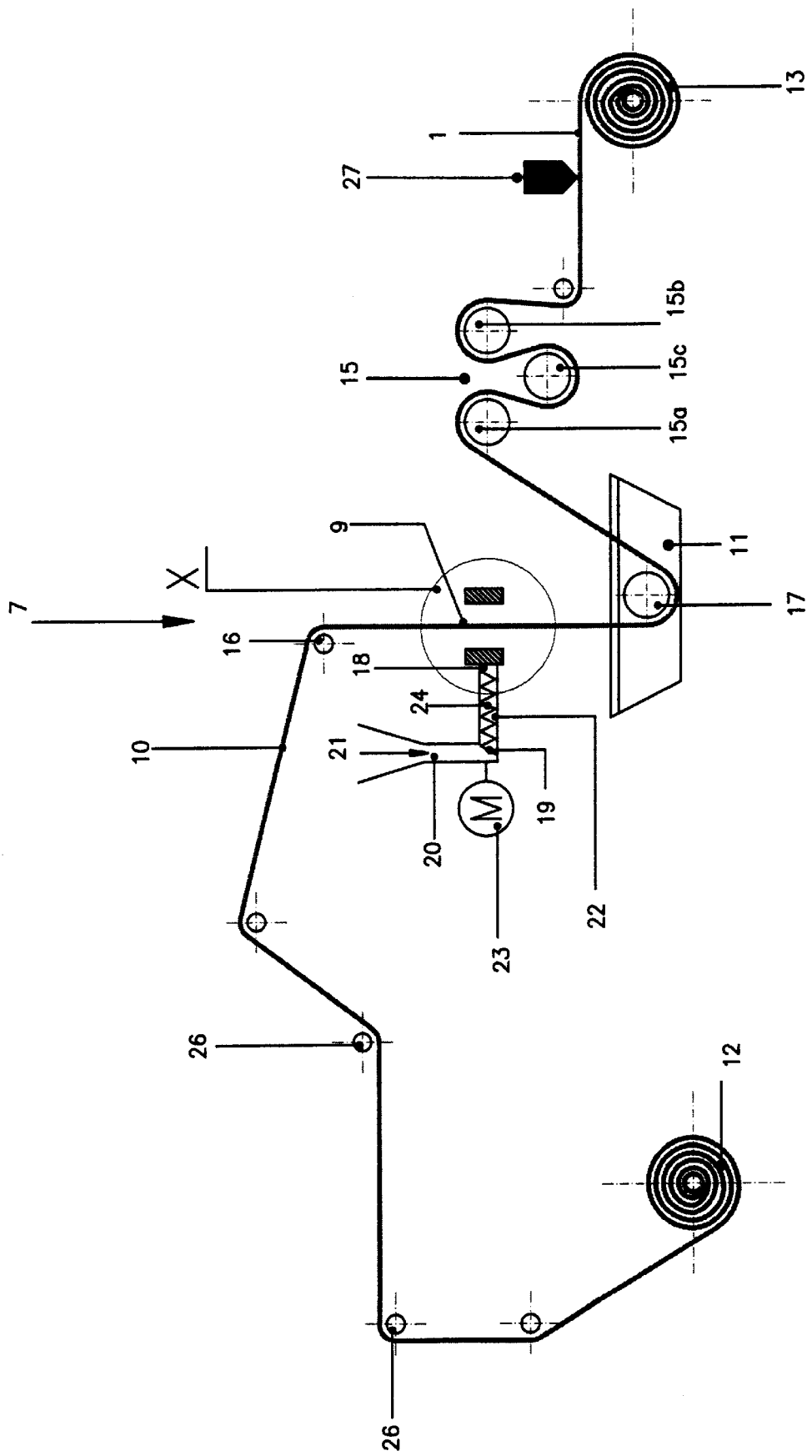
Figure 4A:
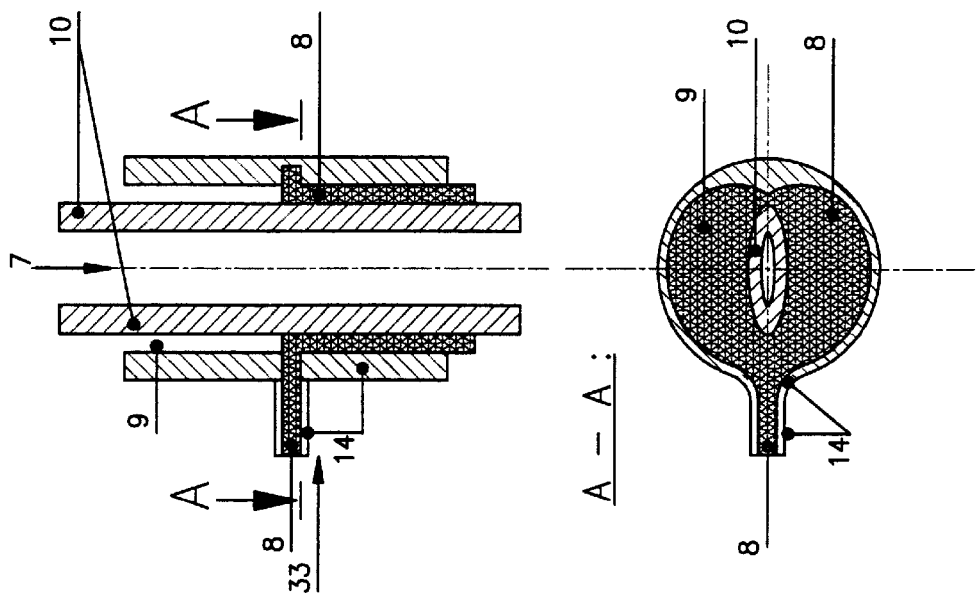
Figure 4A:
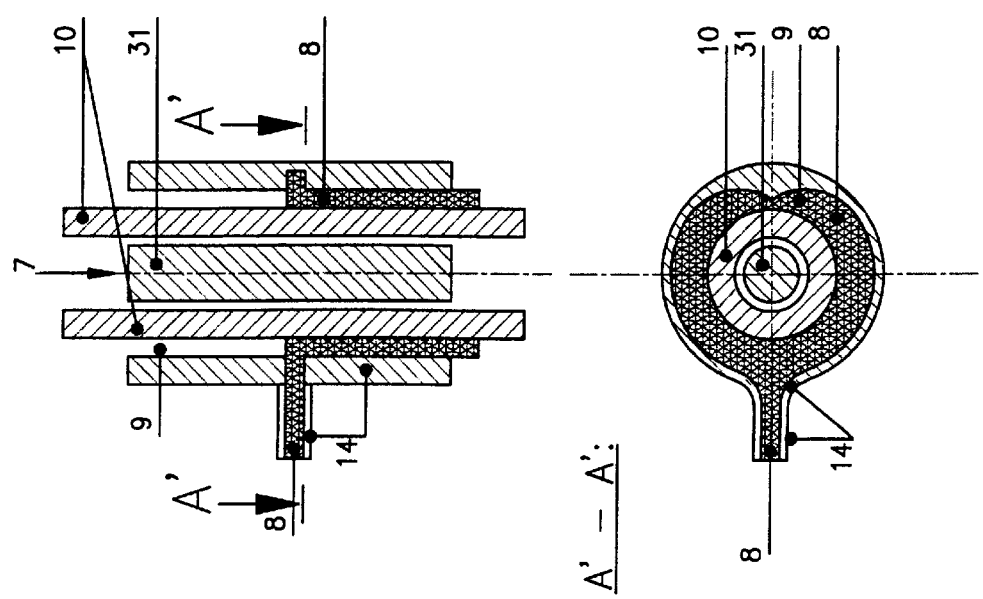

The invention will now be explained according to several figures, in which show:

FIG. 1a a lining operation in curved pipes with a flexible tube according to the prior art;

FIG. 1b a lining operation in curved pipes with a flexible tube according to the invention;

FIG. 2a a top view of a tubular woven fabrics;

FIG. 2b a section B—B of the tubular woven fabrics from FIG. 2a;

FIG. 2c a section C—C of the tubular woven fabrics from FIG. 2a;

FIG. 2d a section C—C of the tubular woven fabrics from FIG. 2a in a stretched condition;

FIG. 3 the course of manufacture of a flexible tube according to the invention;

FIG. 4a a coating tool according to the prior art; and

FIG. 4b views of a coating tool according to the invention;

FIG. 1a shows a pipe 2, in which a flexible tube 1' is introduced turning inside out under an applied pressure. The portions of the flexible tube 1' which are still not turned up, e.g. these ones, which are still not present inside the pipe 2 are provided with a coating (generally of plastic) on the outer side thereof. The inner surface of the flexible tube 1' being still not turned up is provided with an adhesive 28, which adheres to the inner wall of the pipe 2 after flanging of the flexible tube thus forming a durable fixture of the flexible tube toward the pipe 2. However, defective renovations occur in the region of the curvatures 29 of the pipe 2. Wrinkling 36 of the flexible tube according to the prior art occurs inside the region of the inner radius of curvature. Moreover, not complete close fitting of the flexible tube inside the region of the outer radius of curvature (region 35 not being lined) may occur.

FIG. 1b shows the turning up advance of a flexible tube 1 according to the invention, which occurs under a pressure p into the interior of the pipe 2. Here, the inner surface of the turned up flexible tube 1 is brushed with an adhesive 28 for later adhering on the inner pipe wall, the turned up outer surface is provided with a coating of thermoplastic which is pressure sealed and waterproof as well as resistent to chemicals and artificial ageing. Polyurethane elastomer is preferably considered as a material for the coating. The flexible tube is also distinguished in particular by high strength against mechanical loads of any type and comprises the required bursting pressure despite of its high flexibility which thus enables a safe turning inside out still along with a sufficiently high pressure p. The ratio between the bursting pressure of the flexible tube 1 (independently of its turning inside out) and the reversing pressure p to the pressurized turning inside out of the flexible tube 1 into said pipe 2 is preferably within the range between 1.1 and 4.4, particularly preferably between 1.5 and 3.5.

The coating 6 of the flexible tube is introduced radially only to a part of the thickness of fabric and knitted fabrics, respectively, forming a flexible tube blank 10. Hence, it is enabled for the adhesive 28 on the surface opposite to the coating 6 of the fabric and knitted fabrics, respectively, to penetrate sufficiently deep into the fabric and knitted fabrics, respectively. In addition, the fabric and knitted fabrics, respectively, has a good absorbency and penetration power for the adhesive, such that a later travelling behind of the gases (i.e. penetrating of gases into the space between the flexible tube and the pipe) as well as travelling of the gas inside the fabric can be excluded.

The flexible tube 1, inside the curvatures 29 of the pipe 2 as well, closely fits all-over against the inner wall of the pipe beyond the entire perimeter thereof. This requires, in particular with rectangular or acute pipe bends, a very strong linear extension of the flexible tube material in the region of the outer radius of curvature 30 of the inner pipe wall. The flexible tube 1 comprises $\epsilon_{max}$ in the longitudinal direction within the range of 40 to 400%. (as usually, in the present application $\epsilon_{max}$ is defined as the ratio of the maximum length increase to the total flexible tube length with a tension test in breakage time, here a tension force $F_{max}$ is applied to the test sample). For the flexible tube 1, $\epsilon_{max}$ is preferably within the range of 80 to 300% (in comparison: $\epsilon_{max}$ of a flexible tube 1' according to the prior art is between 35 to 40% at maximum.

In addition to the excellent linear extension the flexible tube 1 according to the invention also has a sufficient transversal extension in order to better balance the variations of the inner pipe diameter. With a radial tension load of the flexible tube 1, $\epsilon_{max}$ is within the range between 50 and 100%, preferably within the range between 60 and 90% (depending on the coating thickness). Here, $F_{max}$ is preferably between 50 and 70 N per mm width of the flexible tube. Preferably, the $\epsilon_{max,\ radial}$ to $\epsilon_{max,\ axial}$ ratio is between 1.1 and 10.

At a temperature of 80° C. the bursting pressure is still between 60 and 80% of the bursting pressure at the ambient temperature. From this results, that even at high temperatures during pipe lining, the reversing pressure p is significantly smaller than the bursting pressure of the flexible tube, such that by no means damages of the flexible tube caused by the pressure are allowed to occur.

Obviously, the turning inside out method is not urgently, the flexible tube according to the invention can also be drawn according to other methods such as pulling in, into pipes or ducts (also with non circular e.g. ellipsoidal) cross-section. The outside diameter of the flexible tube 1 may comprise between 9 and 1200 mm, preferably between 12 and 200 mm in the not stretched condition.

In following the structure of the flexible tube 1 is explained in more detail according to the FIGS. 2a to 2c. FIG. 2a shows a fabric made of warp threads 4 and woof threads 5. In FIG. 2a the fabric is shown for the sake of simplicity in a plane condition. A flexible tube blank 10, which comprises the structure of the fabric 3, is woven of warp threads 4 and woof threads 5 on a specific circular loom, wherein the warp threads 4 are contiguously disposed and longitudinally directed in a tubular shape, and one and more woof threads, respectively with respect to the pipe shape are guided helically and in a determined sequence beneath said warp threads 4 therethrogh and beyond these by forming a fabric flexible tube.

Obviously, it is also possible for the flexible tube blank 10 to be manufactured as a knitted fabrics. i.e. to be knitted from yarn. Another possibility is in that to form the flexible tube blank 10 from a substantially square plane fabric or another textile formation such as felt, to form into a tubular shape by joining the longitudinal sides of the square.

The fabric 3 shown in FIG. 2a is performed as a "plain weave". Here, a woof thread 5 is mutually directed below and above of longitudinally directed adjacent warp threads. Obviously, it is also possible to provide other modes of weaving (body weave, atlas weave), such as to lead the woof thread through below several adjacent warp threads and subsequently above several warp threads. Inside the fabric 3, in plane condition thereof, 10 to 1000 warp threads per decimeter, preferably 50 to 300 decimeter are adjacent in a longitudinally directed manner. 10 to 1000 woof threads per decimeter, preferably 50 to 300 per decimeter of unstressed fabric are adjacent in a longitudinally directed manner. With the fabric shown in FIG. 2a three wefts are commonly directed, respectively in parallel, as a weft, preferably, four weft threads or any number of weft threads commonly can be directed in parallel as well as a weft. $\epsilon_{max}$ of the fabric 3 at tension in direction of the warp threads 4 is within the region of 5 to 500%, preferably within the range of 100 to 400%. Particularly characterising for the flexible tube according to the invention is that the warp threads are high resiliently, while the woof threads have a lower elasticity. Here, the ratio of warp threads $\epsilon_{max}$ to woof threads $\epsilon_{max}$ is preferably within the range of 1.1 to 50, it is particularly preferred within the range of 12 to 40.

Aternatively, it is also possible for the flexible tube according to the invention to be manufactured upon a coated knitted fabrics of high resilient yarn, wherein the yarn approximately having the characteristics of the warp threads 4.

The warp threads 4 can be composed of vulcanized elastomers, preferably being of polyurethane yarn. A single warp thread 4 can also be produced as a compound of different materials. For example, it is possible for the warp thread 4 to be composed of one basic warp thread of polyurethane wrapped with a covering yarn made of polyester or polyamide (here, the covering yarn is substantially non resilient, the basis wrap thread is high resilient; when a basic warp thread is used, a multiple covering with covering yarn is to be provided). Here, the basic warp thread, preferably has a length related mass within the range of 22 to 3000 dtex, and the covering yarn has a length related mass of 44 to 1000 dtex. It is possible, for example, for a basic warp thread to be composed of polyurethane yarn having 940 dtex, which is double covered with a covering yarn of polyamide 66 having 78 dtex. A warp thread constructed in this manner is of $\epsilon_{max}$ 450% as well as $F_{max}$ of 9 Newton (measured at breakage of said covering yarns).

According to the embodiment, a basic wrap yarn may be single or multiple covered with a covering yarn. However, all embodiments have in common with $\epsilon_{max}$ of a single warp thread 4 to be within the range of 50 to 500% and $F_{max}$ to be within the range of 1 to 100 Newton (these values for the breaking elongation and breaking load respectively, have been determined with the first cracking of the covering yarns).

The woof threads 5 have a length related mass of 10 to 1000 dtex (preferable 80 to 550 dtex), $\epsilon_{max}$ within the range of 1 to 50% (preferable 8 to 30%) and $F_{max}$ within the range of 1 to 100 Newton (preferable 5 to 34 Newon). For the improvement of the resilient characteristics and absorbency as well, in case the woof threads and warp threads as well can be textured, it is still possible for the threads to be swirled. Polyester yarn is considered to be preferred materials for these woof threads.

FIG. 2b shows a section B—B through the fabric piece from FIG. 2a. Here, a coating 6 is deposited additionally on the upper side of the fabric. This coating 6 consists of a thermoplastic having a high flexibility. In the condition not being coated on a carrier, $\epsilon_{max}$ of the coating is between 80 and 800%, preferable between 300 and 700%. According to the intended purpose, the coating forming the inner wall of a lined pipe and duct, respectively, can be lined with different materials. In the case of gas pipes, for example, the coating can be composed of thermoplastic polyurethane elastomer (TPU). With lining of drinking water supply pipes the use of polyethylene is advantageous. However, thermoplastic polyolefine elastomers can be used as well. TPE (thermoplastic polyether-ester), TPS (thermoplastic styrene-butadiene- and styrene-ethylene-propylene-copolymer, respectively) or TPV (mixtures of polypropylene and crosslinked ethylene-propylene-diene-copolymers) are particularly advantageous.

A coating material being particularly frequently used is a thermoplastic polyurethane-elastomer, which has a high resistance to solvents. This solvent has a modulus of elasticity of 10 MPa, $\epsilon_{max}$ of 450%, stress at break of 30 MPa as well as a hardness of 95 Shore A and 47 Shore D, respectively.

It is particularly apparent from FIG. 2c, why the transversal extension of a flexible tube which is composed of fabric 3, wherein the warp threads being disposed in the longitudinal direction of the flexible tube, is high despite of a rather low elasticity of the woof threads 5 (e.g. at $\epsilon_{max}=$ 12%). With the effect of a pressure burden inside the flexible tube, firstly stretching of the woof thread 5 occurs, wherein warp threads 4 being directed above woof thread are pressed up and high resilient warp threads 4 passing below the woof thread 5 are pressed down (see also FIG. 2d). Thus, the elasticity of the warp threads disposed in the longitudinal direction 7 of the flexible tube also contributes to an improved transveesal extension of the flexible tube 1. In addition to the diameter increase described above by means of forcing away the warp threads by the woof thread 5, bulk up of the flexible tube 1 occurs by means of the rotation of the woof threads 5 itself.

FIG. 3 shows the course of method for manufacturing a flexible tube with high linear extension. A flexible tube blank 10 is reeled up on a reel winder 12. This flexible tube blank 10 consists of a fabric 3 and corresponding knitted fabrics, respectively, being composed of warp threads 4 disposed in the longitudinal direction of the flexible tube blank. This flexible tube is unwound from the reel winder and the flexible tube drum 12, respectively, and guided over flat shaped deflection shafts 26. Thereafter, the flexible tube blank is drawn through a coating chamber 9, in which the outer surface of the flexible tube blank is coated with plastic melting. The flexible tube blank 10 is tensioned between the rollers 16 and 17 such that it has a straight course. The flexible tube blank is merely guided through these rollers and is not supported by means of additional devices in the interior of said flexible tube blank. At the entry of chamber 9 a slot for introducing the flexible tube blank is provided, which is adapted in the form and size of the flat flexible tube blank 10, that only a small gap remains circumferentially between the outer surface of the flexible tube blank as well as the inner slot side. At form and size of the flat flexible tube blank 10, that only a small gap remains circumferentially between the outer surface of the flexible tube blank as well as the inner slot side. At the outlet of the chamber 9 a stripper not shown is arranged, which strips excessive liquid plastic melting by means of two metallic lips pressing upon the small sides of the flat flexible tube blank. Because of this, the coating thickness of the flexible tube 1 and the coated flexible tube blank 10, respectively, is homogenized. The proper function of the chamber 9 as well as of the associated extruder is set forth more properly further below.

After passing through the chamber the flexible tube blank is guided for cooling through a tank filled with water, i.e. a water bath 11. Obviously, other cooling alternatives are possible for the flexible tube being highly heated due to the coating operation, such as by means of glycol or air.

After the flexible tube blank coming out of the water bath 11, it is guided over an exhaust 15 comprising three rollers. Here, the rollers 15a and 15b are stationary supported, while the roller 15c can be moved up and down. The exhaust 15 also generates in addition to the tensioning of the flexible tube a conveying movement of the flexible tube by moving down the roller 15c with the rotation of one of the exhaust rollers, such that the flexible tube blank 10 is drawn through the chamber 9 in the direction 7, hence along the warp threads thereof. After passing through the exhaust, the flexible tube is provided with a character by means of a printing device 27 and wound on a reel winder and the flexible tube drum 13, respectively.

The interior of the chamber 9 is connected through a molten mass pipe 14 with the exit 18 of an extruder 19, which posseses funnel tube and supply means 20, respectively, for thermoplastic raw material such as in the form of ganule. The thermoplastic raw material 21 is guided through the funnel coating art the screw compresses the thermoplastic raw material into plastic melting and guides the melting through the outlet 18 of the extruder toward molten mass pipes 14, which lead into the interior of the chamber 9. Both the extruder 19 and the chamber 9 are provided with several heating means being distributed over the periphery thereof, which generate an increased temperature of the extruder and the chamber as well as the plastic therein.

FIG. 4a illustrates a coating chamber according to the prior art. Here, the flexible tube blank 10 is drawn in the direction 7 through the chamber 9. There, inside the flexible tube blank 10 is a mandrel 31. An extruder not shown supplies plastic melting into the interior of the chamber 9, for example through a cardioid curve shaped molten mass pipes such that the outer surface 10 of the flexible tube is covered with plastic melting 8. As a result of the high pressure inside the chamber 9 the flexible tube blank 10 is pressure loaded from the outside of the flexible tube, such that the inner surface of the flexible tube blank 10 exerts a high pressure upon the mandrel 31. Since the flexible tube blank 10 is drawn through the chamber 9 by means of devices not shown, a strong friction force results in the region of the interface between the inner surface of the flexible tube blank and the mandrel 31, with the friction force is opposed to the force for advancing the flexible tube blank in the direction 7 through the chamber 9. As a result of these opposite forces the flexible tube blank being in the region of the chamber is strongly stretched in the longitudinal direction and coated in this stretched condition. With ceasing the longitudinal stress, the fabric of the flexible tube blank is no longer to be moved back into the unstretched original condition, since the fabric is inhibited by the introduced coating. This results in that, with the method of the prior art, $\epsilon_{max}$ of 35 to 40% would be maximally obtained.

FIG. 4b illustrates a chamber 9 according to the invention. This chamber is substantially circularly constructed and posseses a molten mass pipe 14, which is connected to an extruder outlet not shown. By introducing the plastic melting under pressure in the direction 33, plastic melting 8 passes inside the chamber 9. Above chamber 9 a slot shaped opening is provided for introducing the flat flexible tube blank. A stripper not shown is provided on the lower outlet of the chamber 9 for homogenizing the coating on the coated flexible tube blank 10. The flexible tube blank 10 being not supported in the interior of the flexible tube is guided by means being not shown in detail through the chamber 9 in the direction 7, i.e. longitudinally and in the direction of its warp threads of fabric 3. Here, the outer surface of the flexible tube blank is coated with plastic melting 8 introduced through the molten mass pipes into the interior of the chamber. The plastic melting 8 introduced in the direction 33 is drawn by the movement of the flexible tube blank 10 in the guiding direction 7 along with this guiding direction such that in the upper region of the chamber 9 no further sealing measures are required.

Section A—A in FIG. 4b shows a cross-section through the chamber 9. Here, it is to be seen, how the flexible tube blank 10 is flat compressed due to the affect of the plastic melting introducing in the interior of the chamber and remains in its substantially plane condition, respectively. In the present embodiment the cross-section of chamber 9 being substantially circularly constructed, however, it is also possible for the chamber 9 to be constructed transversely to the longitudinal direction of the advanced flexible tube blank 10 into a cross-section being substantially ellipsoidal corresponding to the cross-section of the compressed flexible tube blank.

The molten mass pipes 14 which lead in the interior of the chamber may comprise various forms in the end portion, i.e. ins the close region oriented towards the outside of the flexible tube blank 10. It is possible the molten mass pipes to be constructed along the inner wall of the chamber as a cardioidal curve extending from the outlet of the extruder 18. However, it is advantageous to feed the plastic melting in form of a spiral distributor to the surface of the flexible tube blank. Here, it is always ensured, that the path of the plastic melting from the outlet of the extruder 18 to each point on the outer periphery of the flexible tube blank 10 has approximately the same length. Here, the formation of clearance volumes of the plastic melting 8 is avoided.

Since the flexible tube blank 10 is guided in the interior of the flexible tube in a not supported manner through the chamber, relative movement and hence friction in the interior of the flexible tube blank do not originate, which could lead to a linear extension of the flexible tube blank. Thus the flexible tube blank 10 being in almost not stretched condition is deposited with plastic melting 8, which cools to the coating 6. Hence, it is possible for a flexible tube blank, which comprises high resilient warp threads being longitudinally oriented to be coated in a manner such that after such coating operation, practically, the longitudinal extensibility of the flexible tube blank can be fully used. Thus, for example with a flexible tube blank having $\epsilon_{max}$ in the range of 300 to 350% in the longitudinal direction, $\epsilon_{max}$ of the coated flexible tube of 250 to 300% can be obtained without any problems such as using thermoplastic polyurethane elastomer as a coating material. Such high elasticities can be obtained with maintaining a very smooth and non-porous surface, the surface quality of the coating is significantly improved with the method according to the invention in contrast to the introductory described dip coating method or plain coating method.

What is claimed is:

1. A flexible tube for lining pipes and ducts, which is introduced into a pipe, wherein said flexible tube is composed of coated fabric having high resilient warp threads as well as woof threads wherein the ratio of the warp threads $\epsilon_{max}$ to woof threads $\epsilon_{max}$ is within the range of 1.1 to 50.

2. A flexible tube for lining pipes and ducts, which is introduced into a pipe, wherein said flexible tube is composed of a coated knitted fabric having high resilient yarn, wherein the $\epsilon_{max}$ of the flexible tube is longitudinally within the range of 40 to 400%.

3. A flexible tube according to claim 1, wherein the warp threads are composed of polyurethane yarn.

4. A flexible tube according to claim 1, wherein one warp thread consists of one basic warp thread of polyurethane being wrapped with winding yarn composed of polyester or polyamide.

5. A flexible tube according to claim 1, wherein one warp thread consists of one basic warp thread being wrapped with a covering yarn, wherein said basic warp thread comprises a longitudinally related mass within the range of 22 to 3000 dtex and the covering yarn comprises a longitudinally related mass of 44 to 1000 dtex.

6. A flexible tube according to claim 1, wherein said warp thread is composed of a basic warp thread being multiply wrapped with covering yarn.

7. A flexible tube according to claim 1, wherein $\epsilon_{max}$ of a single warp thread is within the range of 50 to 500% and $F_{max}$ thereof is from 1 to 100 N.

8. A flexible tube according to claim 1, wherein the woof thread is composed of polyester yarn.

9. A flexible tube according to claim 1, wherein the woof thread is textured or interlaced.

10. A flexible tube according to claim 1, wherein the woof thread has a longitudinally related mass of 10 to 1000 dtex, $\epsilon_{max}$ within the range of 1 to 50% and $F_{max}$ within the range of 1 to 100 N.

11. A flexible tube according to claim 1, wherein a woof thread is mutually guided below and above of longitudinally directed adjacent warp threads.

12. A flexible tube according to claim 1, wherein the fabric has a surface plane with a density of 10 to 1000 longitudinally directed adjacent warp threads per dm and 10 to 1000 longitudinally directed woof threads per dm.

13. A flexible tube according to claim 1, wherein $\epsilon_{max}$ of said fabric under tension towards said warp threads is within the range of 5 to 500%.

14. A flexible tube according to claim 1 or 2, wherein the fabric is coated with a thermoplastic having high flexibility.

15. A flexible tube according to claim 1 or 2, wherein said flexible tube is coated with a thermoplastic polyurethane elastomere.

16. A flexible tube according to claim 1 or 2, wherein $\epsilon_{max}$ of the coatring is within the range between 80 and 800% when in the condition being not coated upon a carrier.

17. A flexible tube according to claim 1 or 2, wherein the coating of said flexible tube is radially introduced only up to a part of the fabric thickness.

18. A flexible tube according to claim 1 wherein the $\epsilon_{max}$ of the flexible tube is longitudinally within the range of 40 to 400%.

19. A flexible tube according to claim 1 or 2, wherein a ratio between the bursting pressure of the flexible tube and the reversing pressure for pressurized turning inside out the flexible tube into a pipe is within the range between 1.1 and 4.4.

20. A flexible tube according to claim 1 or 2, wherein the outside diameter of the flexible tube being in not stretched condition is between 9 and 1200 mm.

21. A flexible tube for lining pipes and ducts, which is introduced into a pipe, wherein said flexible tube sic composed of coated fabric having high resilient warp threads as well as woof threads wherein the $\epsilon_{max}$ of the fabric under tension toward said warp threads is within the range of 5 to 500%.

22. A flexible tube for lining pipes and ducts, which is introduced into a pipe, wherein said flexible tube sic composed of coated fabric having high resilient warp threads as well as woof threads wherein the $\epsilon_{max}$ of the flexible tube is longitudinally within the range of 40 to 400%.

* * * * *